US006621574B1

(12) United States Patent
Forney et al.

(10) Patent No.: US 6,621,574 B1
(45) Date of Patent: Sep. 16, 2003

(54) DUAL FUNCTION SAFETY AND CALIBRATION ACCESSORY FOR RAMAN AND OTHER SPECTROSCOPIC SAMPLING

(75) Inventors: Robert W. Forney, Waltham, MA (US); Nancy T. Kawai, S. Easton, MA (US)

(73) Assignee: InPhotonics, Inc., Norwood, MA (US)

( * ) Notice: Subject to any disclaimer, the term of this patent is extended or adjusted under 35 U.S.C. 154(b) by 0 days.

(21) Appl. No.: 09/578,975

(22) Filed: May 25, 2000

(51) Int. Cl.[7] .............................. G01J 3/44; G01J 1/10; G01N 21/01; G02B 27/00; G01D 18/00
(52) U.S. Cl. .................... 356/301; 356/243.1; 356/244; 359/894; 250/252.1
(58) Field of Search .................. 356/301, 386, 356/243.1–243.8, 244; 250/252.1; 359/506, 894; 73/1.01

(56) References Cited

U.S. PATENT DOCUMENTS

| | | | | |
|---|---|---|---|---|
| 3,885,879 A | * | 5/1975 | Louder et al. | 250/227.28 |
| 4,050,450 A | * | 9/1977 | Polanyi et al. | 356/243.5 |
| 4,082,464 A | * | 4/1978 | Johnson, Jr. | 356/418 |
| 4,575,629 A | * | 3/1986 | Schnell et al. | 250/238 |
| 5,452,084 A | * | 9/1995 | Mitchell et al. | 250/282 |
| 5,850,623 A | * | 12/1998 | Carman et al. | 250/252.1 |
| 6,151,111 A | * | 11/2000 | Wechsler et al. | 356/318 |

* cited by examiner

Primary Examiner—Zandra V. Smith
Assistant Examiner—Gordon J Stock

(57) ABSTRACT

This invention relates to an accessory for incorporation into Raman and other spectroscopic instruments for combining shuttering and spectroscopic calibration functions. The accessory is comprised of an assembly with at least two positions that may be inserted into the light path, one position allowing light to be directed to and from the sample, and another position containing a reference standard that blocks the beam and provides a shuttering function. When the light strikes the reference standard, a reference spectrum is produced that may be used to calibrate the spectrograph. The device is especially useful in combination with compact sampling accessories for Raman spectroscopy.

12 Claims, 5 Drawing Sheets

POSITION 1

POSITION 2

DUAL FUNCTION SAFETY AND CALIBRATION ACCESSORY FOR RAMAN AND OTHER SPECTROSCOPIC SAMPLING

CROSS REFERENCE TO RELATED APPLICATIONS

Not Applicable

FEDERALLY SPONSORED RESEARCH

Not Applicable

SEQUENCE LISTING OR PROGRAM

Not applicable

BACKGROUND OF THE INVENTION—FIELD OF THE INVENTION

This invention relates to accessories for Raman spectroscopy and other light-stimulated spectroscopic techniques, such as fluorescence, phosphorescence and light scattering, which prevent operator exposure to intense light sources and also provide standard signals for calibration of the spectroscopic instrumentation.

BACKGROUND OF THE INVENTION

Raman spectroscopy is a technique for characterizing materials according to the frequency of their molecular vibrations. The basic measurement entails irradiating a sample with a monochromatic light source—typically a laser—and analyzing the spectroscopic distribution of the scattered light. Raman spectra are obtained as a series of lines at both higher and lower wavelengths with respect to the exciting source. Typically the spectra are many orders of magnitude weaker in intensity than the exciting source, so the measurements are usually made with relatively intense lasers. These light sources present potential safety hazards to the human eye and skin. Hence, in order for Raman spectroscopic instruments to be used safely, means are required to prevent exposure of personnel to the exciting source beam.

Another requirement of Raman spectroscopic instrumentation is to make measurements with the highest possible accuracy and reproducibility. In order to develop a correlation of the Raman spectra with the molecular bonding and structure of the sample, the wavelengths of the Raman peaks and their relative intensities need to be known with a high degree of certainty. Spectra are measured with a spectrograph that separates the light according to wavelength and directs it onto a detector. Detectors and spectrograph optics, such as diffraction gratings, typically have a response that is wavelength dependent. In addition, the correlation between wavelength and the position of optical elements needs to be determined empirically before the spectrograph can be used for accurate assignment of peak wavelengths. The process of characterizing a spectrograph with respect to the wavelength dependence of measured light intensity and to the correlation between wavelength and position of the optical elements is known as calibration and is carried out using optical standards. Calibration may be effected for example by exposing the input of the spectrograph to standard light sources. To calibrate the instrument with respect to the wavelength dependence of spectral response, a broadband light source with a well-characterized intensity versus wavelength is employed. Calibration for wavelength versus position is usually done by obtaining with the spectrograph spectra of standard materials having one or more sharp spectral lines of precisely known wavelength. For prior art describing calibration of Raman spectrometers, see for example U.S. Pat. Nos. 5,850,623, 5,652,653 and 5,452,084.

Shutters are well-known in prior art as safety features in laser-based instrumentation, and are required by various regulatory agencies. However, as Raman and related optical instruments like fluorimeters, fluorescence microscopes, particle size analyzers and luminometers become more portable, there is a necessity of combining functions. The functions of spectral calibration for wavelength and intensity are typically done by some separate external component such as standard lamps or samples. Instruments need to be calibrated frequently to accommodate minute changes in the positions of optics and detector response that occurs due to environmental factors, component aging, jarring, etc. Thus, there is a general need to include calibration functions within the instrument, and to do so without sacrificing compactness.

A particularly favorable configuration for Raman sampling is the fiber optic Raman probe, see, for example, U.S. Pat. Nos. 5,112,127, 5,911,017, 4,573,761 and 5,978,534. Such probes enable the sample to be at some distance from the spectrograph. In U.S. Pat. No. 5,112,127, for example, laser light is conducted down one optical fiber, focused onto the sample, the scattered light collected with suitable optics, focused into one or more optical fibers, and conducted back to the spectrograph and detector. Fiber optic samplers can present new hazards because of the possibility of the user looking into the distal end. In some fiber optic sampling accessories, the light coming out of the distal end of the sampling apparatus is in a parallel (collimated) form that, on impacting the eye, will become focused onto the retina in a small spot that can readily cause retinal burning. Furthermore, fiber optic samplers are meant to allow users to address samples in small spaces, such as reaction vessels and inside crevices. Hence, it is desirable to build shutters and calibrators into fiber optic sampling accessories without greatly increasing the size and weight.

SUMMARY OF THE INVENTION

The object of the invention is to provide an opto-mechanical accessory that can be used with laser-based spectrograph instruments, such as Raman spectrographs, that enables both safe operation and spectral calibration. While the invention can be adapted to most if not all Raman spectrographs, it is particularly adaptable to inclusion into compact fiber optic Raman sampling probes. The basic component comprises a structure with at least two positions, which may be introduced into the optical beam path prior to the sample. The first position contains an opening, an offset assembly or a transmissive optical element such as a neutral density filter that permits the light source to illuminate the sample. The second position contains a material or component that provides a signal that can be used to calibrate the spectrographic instrument. This material/component can be a substance that gives a standard Raman or luminescence spectrum in response to the optical source. The standard spectrum may be recorded whenever a calibration is required. Multiple positions can be used to introduce different standards into the optical path. The open position is used only during spectral measurement of the sample, thus avoiding operator exposure at other times.

The standard could also be an active emissive light source with a known spectral distribution. Possible active light sources include light emitting diodes, semiconductor lasers, incandescent lamps. Thin film organic light emitting diodes are especially compact sources that could be integrated into the assembly of this invention.

The invention is particularly useful as an accessory for Raman spectroscopy. A common component for Raman spectroscopy is the fiber optically coupled sampling probe that can, for example, be immersed in a reaction mixture or process stream to monitor chemical composition. The accessory can be incorporated into such a probe as a sliding bar or rotating wheel for introducing open and calibrate positions into the optical beam. The calibrate position may have a material such as a polyfluorinated hydrocarbon that gives a sharp, characteristic Raman spectrum. It may also have a luminescent material such as commercial green bottle glass that responds to the laser source that provides a broad output of well-known intensity distribution.

DESCRIPTION OF PREFERRED EMBODIMENTS

Figure 1:
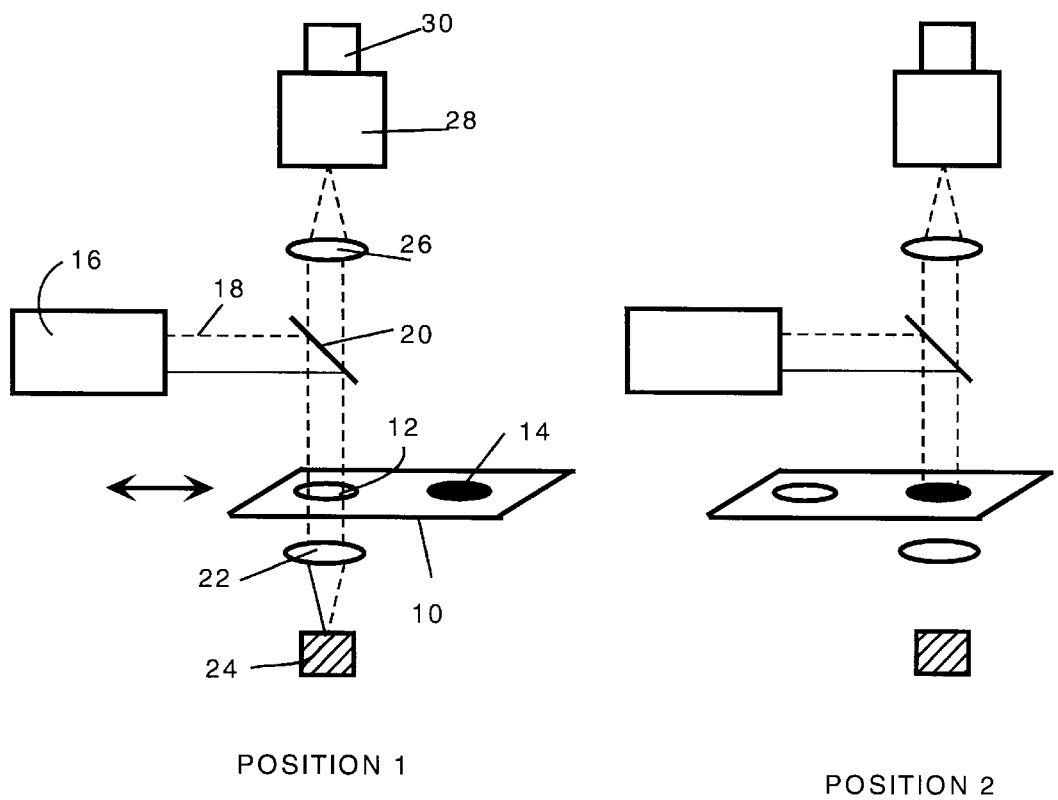
FIG. 1 is a schematic diagram showing a generic optical configuration employing the accessory with both shuttering and standardizing functions.

A generic setup for conducting Raman, luminescence or other light-stimulated spectroscopy on a sample is shown in FIG. 1 along with one embodiment of the opto-mechanical element of this invention. The setup incorporates a sliding assembly 10 that has in one position an aperture 12 and in another position a reference material 14. A laser source 16 with collimator optics that render the beam parallel and non-divergent sends out a collimated monochromatic light beam 18. A dichroic beam splitter 20 receives the beam, reflecting the monochromatic laser source wavelength and shorter wavelengths in the direction of the sliding assembly 10. With the assembly in Position 1, light is admitted through aperture 12 to a lens 22, which focuses the light onto the sample 24. In this backscattering configuration, light scattered from the sample within the collection field of lens 22 is directed back up through the aperture 12 and onto the beam splitter. Light of wavelength longer than the source laser wavelength passes through the beam splitter and is focused by imaging lens 26 onto the slit of a spectrograph 28. There the light is dispersed into its spectral components and converted into electrical signals by a detector 30.

When the assembly is in Position 2, the beam reflected off the beam splitter is directed onto a reference material 14 instead of the sample. The reference material is selected to produce a signal that may be used for calibration of spectral intensity, wavelength or both. Light scattered off and/or emitted from the reference material is directed through the beam splitter, where the reference spectrum is transmitted and focused into the input aperture of the spectrograph.

Alternate embodiments of the invention are a rotating wheel with apertures and reference standards or a multi-element linear slide. The slide, wheel or other mechanism for positioning can be operated manually or using positioning motors under manual or computer control. The assembly may be placed in a collimated or focused part of the optical path. For example, in FIG. 1, the sliding assembly may be placed in a position between lens 22 and sample 24.

Several different types of reference materials may be used. The material may be a Raman scatterer with sharp lines. Examples of reference materials with strong and sharp Raman spectra include diamond, polyethylene, fluorocarbons, and solid aromatic hydrocarbons such as naphthalene. The reference may also produce a well-characterized fluorescence or phosphorescence in response to irradiation from the monochromatic beam; see, for example, "Calibration of Raman spectrometer instrument response function with luminescent standards", by K. Frost and R. McCreery, Appl. Spectroscopy 52, 1614 (1998). In this case, the reference materials must absorb the monochromatic light in either a single or multi-photon process. Hence, different reference materials will be appropriate for different laser wavelengths. Examples of luminescent reference materials include Kopp type 2412 filter glass and standard commercial green bottle glass for Raman spectrometers using 782 nm (diode laser) excitation, and coumarin dye for 514.5 (Ar ion laser) excitation. Dyes may be dissolved in a transparent polymer matrix such as polymethylmethacrylate in order to provide coupons that can be incorporated into the sliding assembly 10, rotating wheels, or other mechanical elements designed for the purposes of this invention. A broadband luminescent standard may be combined with a Raman standard to provide both instrument response and wavelength calibration in the same standard.

Figure 2:
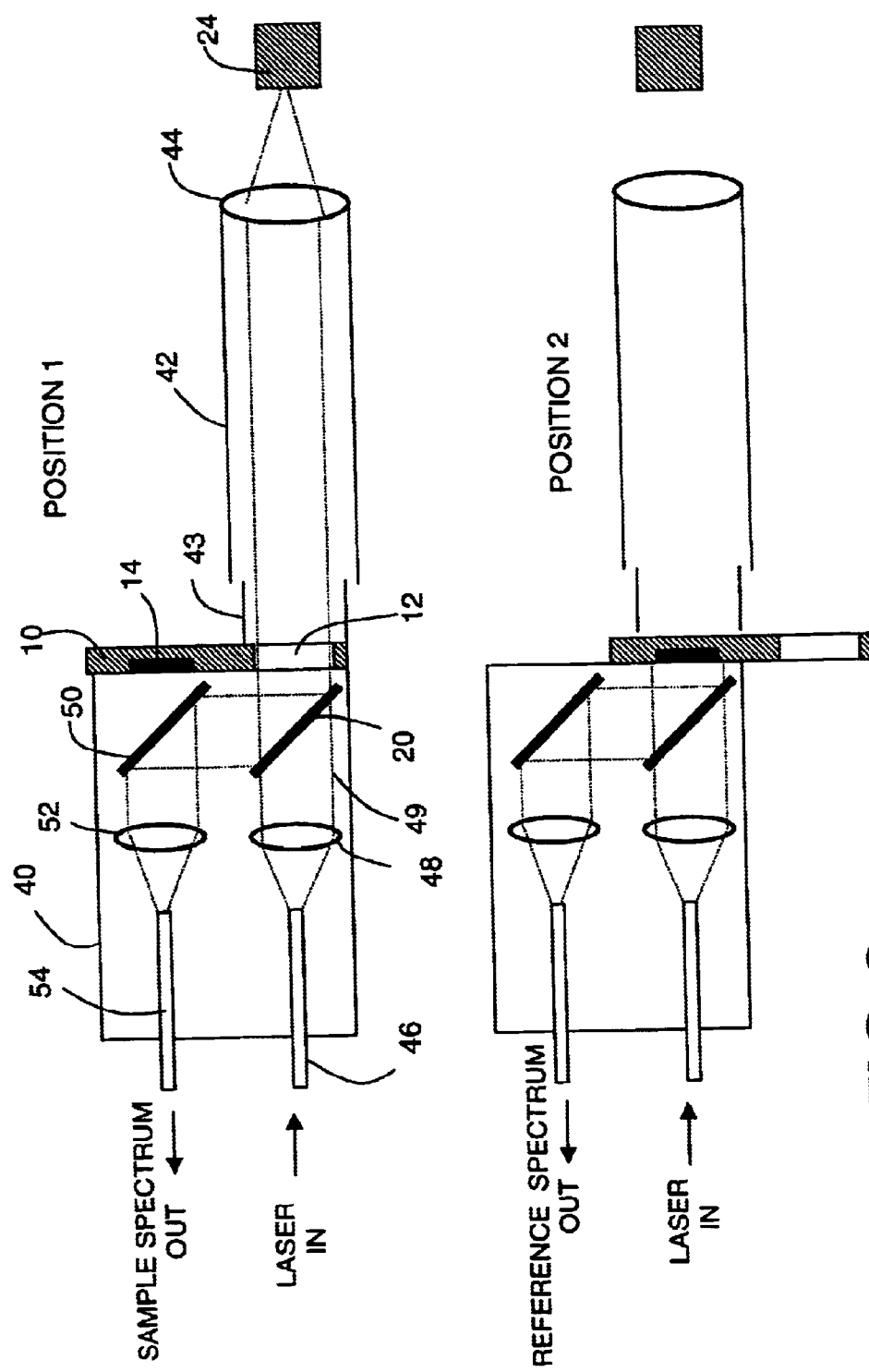
FIG. 2 is a schematic diagram showing the inclusion of an accessory of this invention into a fiber optic Raman probe head of prior art with a detachable extension.

A preferred embodiment is to incorporate the assembly into a fiber optic Raman probe. FIG. 2 shows a fiber optic sampling probe of prior art, which has also a two-position sliding assembly shutter and calibration standard 10. The operation of this enhanced probe is as follows. The probe optics, at the terminus of optical fibers for delivering light to and collecting light from the sample, are enclosed in a housing 40, which has the provision for attaching an extension tube 42 at the exit aperture 43. The extension tube enables light to be directed into a small, confined or reactive space, such as a chemical reaction vessel or a vacuum system, where light is focused onto the sample 24 by lens 44 at the distal end of the tube. In operation, exciting laser light transmitted by optical fiber 46 is collimated by lens 48. The parallel collimated light 49 is directed onto beam splitter 20 which transmits the laser wavelength. When the assembly 10 is in Position 1, the parallel light passes through aperture 12 into the extension tube and is focused onto the sample 24. Light scattered off the sample is collected by collimating lens 44. The parallel return light encounters beam splitter 20, which reflects light of longer wavelength than the exciting laser light, this light containing the desired Raman spectrum. A mirror 50 reflects the light at 90°. The light then is focused into return optical fiber 54, which directs it to a spectrometer. (This particular optical arrangement allows the input and output fibers to be parallel, facilitating construction of a small cylindrical probe head.) With assembly 10 in Position 2, the calibration standard 14 is in the path of the light beam, thus stopping the beam from exiting aperture 43. With assembly 10 in this position, hazardous collimated light is prevented from striking the eyes of the user. The user can then conveniently attach and detach extension 42. At the same time, the laser light is back-scattered by reference material 14 onto beam splitter 20. The reference spectrum, e.g. of a fluorocarbon standard, is directed to output optical fiber 54, and to the spectrograph, where it is recorded. The spectral lines of the standard are used to assign absolute frequencies to the lines of the sample.

EXAMPLE

Figure 3:
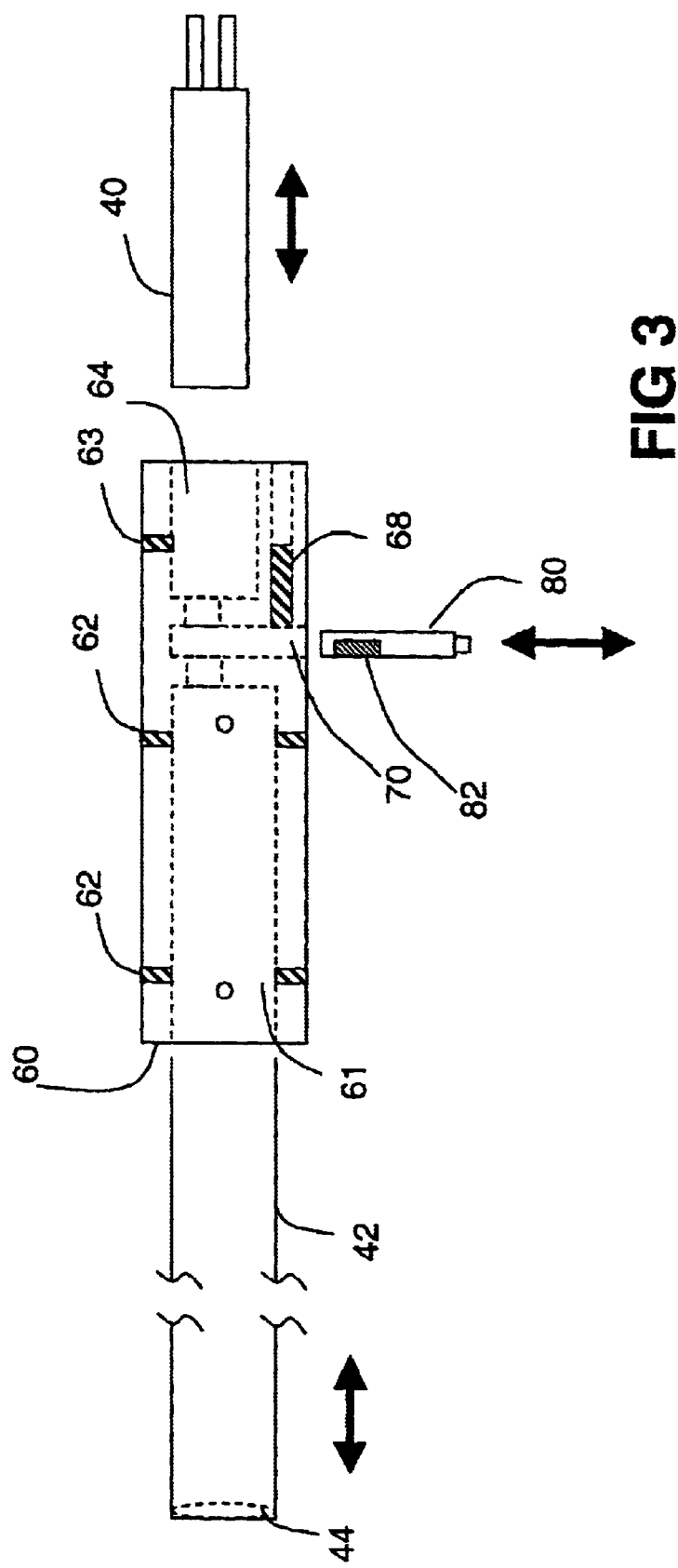
FIG. 3 is a drawing showing an assembly accommodating a commercial Raman probe, a sliding assembly of this invention and an optical extension tube.
Figure 4:
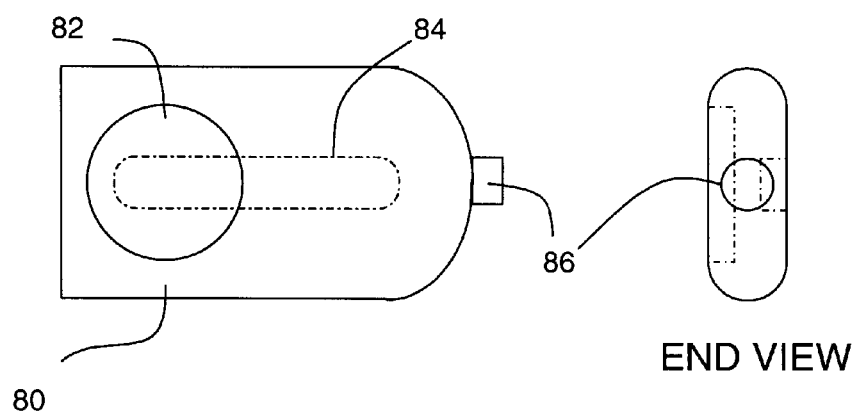
FIG. 4 is a detail view of one embodiment of the sliding assembly.

Dual Function Shutter and Wavelength Standard Incorporating Commercial Raman Probe A two position shutter and calibration apparatus was assembled according to FIG. 3 as a coupler between a commercial fiber optic Raman probe and an extension tube used to access chemical process reactors. The machined stainless steel cylindrical adapter 60 is provided with a cylindrical holder 61 at one end for an extension tube 42 and a cylindrical holder 64 at the other end for the Raman probe 40. The extension and probe are held in place by positioning screws 62 and 63. A slot 70 is provided for a two-position stainless steel slide assembly 80 incorporating a calibration element 82. In the pushed-in position, the assembly presents the calibration element to the optical beam path, while in the pulled-out position the optical path is open, allowing the excitation and return light beams to pass through the extension tube 42 to and from the sample. In FIG. 4 detail of the assembly 80 shows the calibration standard 82 (Teflon), a track 84 for a tensioning screw (FIG. 3, 68) to hold the assembly in position and optionally a finger holder 86.

Figure 5:
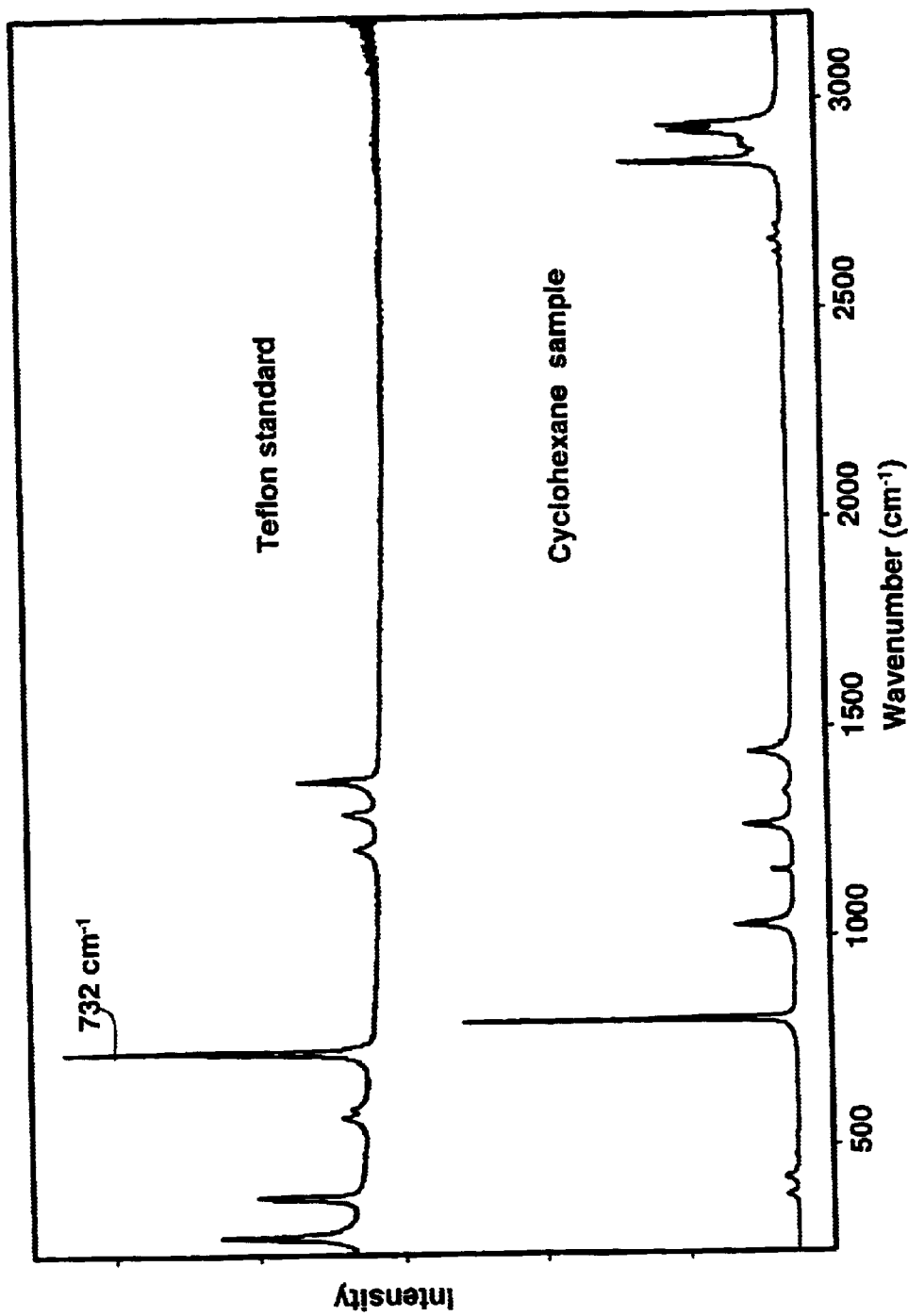
FIG. 5 are Raman spectra of a sample (cyclohexane) obtained with the assembly in the pulled out position and the reference (Teflon) with the assembly in pushed in position.

To demonstrate operation the apparatus in FIG. 3 was connected as a sampling probe to a commercial Raman spectrograph (InPhotonics RS 2000) and a diode laser source operating at 785 nm. The the slide assembly was pushed in and a spectrum recorded of the Teflon standard, shown in FIG. 5. Next, the extension tube was immersed in cyclohexane, and a spectrum was recorded as in FIG. 5 with the slide assembly in the pulled-out position. The Teflon standard provided precise calibration wavelengths, for example at 732 $cm^{-1}$, which in turn were used to assign precise wavelengths to the cyclohexane sample peaks. The calibration standard can be recorded at any time before or after obtaining sample spectra.

The specifications described herein should not be considered to limit the scope of this invention, but instead to serve as illustrations of certain preferred embodiments. For example, there are numerous possibilities for the shapes and structures of the elements of the assembly and designs for including the assemblies into spectroscopic sampling accessories. In addition, other optical and mechanical elements can be added to the structure to enhance its operation. Thus the scope of the invention should be determined by the appended claims rather than the specific examples given.

What is claimed is:

1. An assembly for obtaining calibrated Raman spectra over optical fibers and for ensuring eye safety said assembly comprising:
   a) a Raman sampling probe at the terminus of optical fibers for conducting monochromatic light to a sample and/or for returning light scattered off the sample to a spectrograph,
      said monochromatic light exiting the distal end of the probe, illuminating the sample, and the light scattered from the sample also collected at the distal end of the probe in a backscattering geometry, and
   b) a moveable aperture in the optical path between the distal end of the sampling probe and the sample with at least two mechanically interchangeable positions:
      a first position containing an opening or transmissive optical element permitting the monochromatic light to illuminate the sample and backscattered light to be collected by the probe and returned to the spectrograph to produce a sample spectrum, and
      a second position blocking light to the sample and to the eye and further placing in the optical path an optical standard that delivers to the probe a standard spectrum which is returned to the spectrograph for instrument calibration.

2. The assembly of claim 1 wherein the optical standard is a luminescent standard that when illuminated with the monochromatic light produces a luminescence spectrum with known spectral distribution of intensity versus wavelength.

3. The assembly of claim 2 wherein the luminescent standard is green bottle glass.

4. The assembly of claim 1 wherein the optical standard is a Raman scattering material that when illuminated with the light source produces a Raman spectrum with known spectral distribution of Raman peak wavelengths.

5. The assembly of claim 4 in which the Raman scattering material standard is Teflon.

6. The assembly of claim 1 wherein the optical standard is a combination of a standard luminescent material and a standard Raman scattering material.

7. The assembly of claim 1 wherein the optical standard is a light absorbing material with negligible optical scattering or emission.

8. The assembly of claim 1 wherein the optical standard is an emissive light source with a known spectral distribution.

9. The assembly of claim 1 wherein the moveable aperture is a wheel with rotational to positions for introducing transmissive elements or standards in the light path.

10. The assembly of claim 1, wherein the moveable aperture is a sliding bar to position said aperture or standards in the optical path.

11. The assembly of claim 1, further incorporating:
   an adaptor tube with an insert at one end for an optical extension tube for addressing the sample and another insert at the other end for accepting the distal end of the Raman probe, and in the adaptor tube body separating the two inserts a slot incorporating a slide assembly with at least two positions:
      the slide assembly in a first position having on its surface the optical calibration standard;
      the slide assembly in a second position having the opening or transmissive optical element.

12. The assembly of claim 11, in which the slot extends completely through the adaptor tube body in order to incorporate a slide assembly with multiple positions for a multiplicity of standards and transmissive optical elements.

* * * * *